United States Patent
Lefman et al.

(10) Patent No.: US 9,492,249 B1
(45) Date of Patent: Nov. 15, 2016

(54) DENTAL TOOL

(71) Applicants: Jonathan Alan Lefman, Newton, MA (US); David Gil Bloom, Boca Raton, FL (US)

(72) Inventors: Jonathan Alan Lefman, Newton, MA (US); David Gil Bloom, Boca Raton, FL (US)

( * ) Notice: Subject to any disclaimer, the term of this patent is extended or adjusted under 35 U.S.C. 154(b) by 25 days.

(21) Appl. No.: 14/639,626

(22) Filed: Mar. 5, 2015

Related U.S. Application Data

(60) Provisional application No. 61/948,082, filed on Mar. 5, 2014.

(51) Int. Cl.
   *A61C 3/14*      (2006.01)
   *A61C 8/00*      (2006.01)
   *A61C 1/12*      (2006.01)

(52) U.S. Cl.
   CPC .............. *A61C 8/0089* (2013.01); *A61C 1/12* (2013.01); *A61C 8/005* (2013.01)

(58) Field of Classification Search
   CPC ........................ A61C 8/0087; A61C 8/0089
   See application file for complete search history.

(56) References Cited

U.S. PATENT DOCUMENTS

| | | |
|---|---|---|
| 5,622,500 A | 4/1997 | Niznick |
| 2009/0305191 A1 | 12/2009 | Jandali |
| 2010/0062390 A1 | 3/2010 | Hetsroni |
| 2013/0004916 A1 | 1/2013 | Bellanca et al. |

FOREIGN PATENT DOCUMENTS

WO    2009045013 A1    4/2009

*Primary Examiner* — Brian T Gedeon
(74) *Attorney, Agent, or Firm* — Ulmer & Berne LLP

(57) ABSTRACT

Dentals tools are provided for assisting with the gripping and manipulation of an abutment during a dental procedure. A dental tool can have a resilient collar that defines a central bore for frictionally receiving the abutment. Once inserted into the central bore, the dentist can transport the abutment to a worksite within a patient's mouth.

22 Claims, 24 Drawing Sheets

DENTAL TOOL

CROSS REFERENCE TO RELATED APPLICATION

This application claims the benefit of U.S. provisional patent application Ser. No. 61/948,082, filed on Mar. 5, 2014, entitled, DENTAL TOOL, the disclosure of which is hereby incorporated by reference in its entirety.

TECHNICAL FIELD

The systems and methods described below relate generally to the field of dental implants. More particularly, the systems and methods relate to devices for maintaining the relative placement of an abutment during attachment of the abutment to an implant.

BACKGROUND

A typical dental process includes a series of steps performed by a dentist. First, an incision is made in a patient's gingiva to expose bone. Using a high-speed drill, a pilot hole is made in the jaw to set up subsequent drilling steps. Next, using a low-speed drill, the diameter of the pilot hole is enlarged incrementally. When the hole is sized appropriately, a titanium implant is then threaded into the hole in the bone. Osseointegration, the intimate contact of bone to implant, allows the implant to bear the load of the subsequently placed abutment and restoration. Following osseointegration, an abutment is attached to the implant, using a screw. The exposed portion of the abutment generally sits above the gum line. Finally, a crown is cemented to the abutment.

The attachment of the abutment to the implant can be relatively difficult due to a number of factors. For example, the abutment and the abutment fastener (such as a screw), are both small, making them difficult for the dentist to manipulate and handle. Additionally, abutments are often attached to an implant that is positioned in the rear of the jaw thereby making the implant difficult to access.

There is therefore a need for a dentist to have a tool to assist with the abutment placement and attachment process.

BRIEF DESCRIPTION OF THE DRAWINGS

The present disclosure will be more readily understood from a detailed description of some example embodiments taken in conjunction with the following figures.

DETAILED DESCRIPTION

Figure 1:
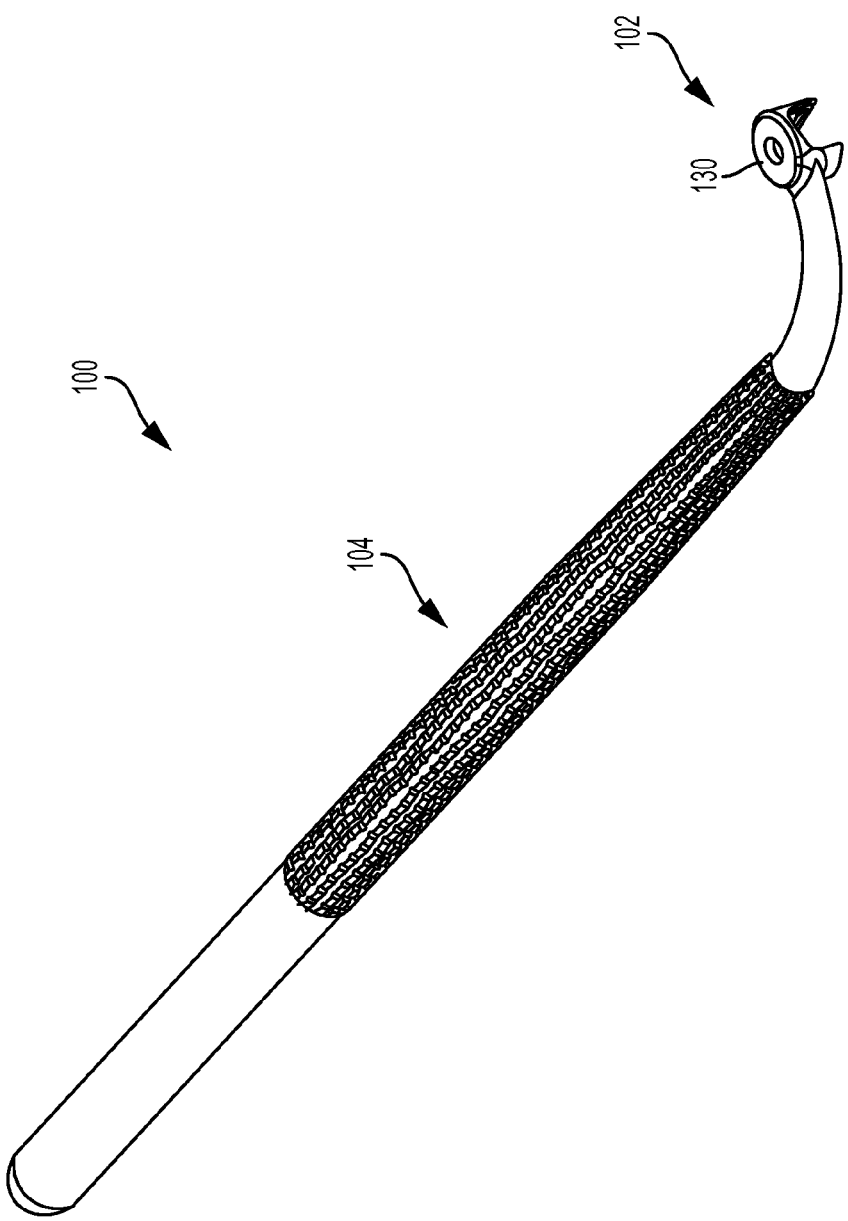
FIG. 1 depicts a perspective view of an example dental tool with the resilient collar removed for clarity.

Various non-limiting embodiments of the present disclosure will now be described to provide an overall understanding of the principles of the structure, function, and use of the dental tools disclosed herein. One or more examples of these non-limiting embodiments are illustrated in the accompanying drawings. Those of ordinary skill in the art will understand that devices and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

The devices and methods disclosed herein are described in detail by way of examples. The examples discussed herein are examples only and are provided to assist in the explanation of the devices and methods described herein. None of the features or components shown in the drawings or discussed below should be taken as mandatory for any specific implementation of any of these devices and methods unless specifically designated as mandatory. For ease of reading and clarity, certain components or methods may be described solely in connection with a specific figure. In this disclosure, any identification of specific techniques, arrangements, etc. are either related to a specific example presented or are merely a general description of such a technique, arrangement, etc. Identifications of specific details or examples are not intended to be, and should not be, construed as mandatory or limiting unless specifically designated as such. Any failure to specifically describe a combination or sub-combination of components should not be understood as an indication that any combination or sub-combination is not possible. It will be appreciated that modifications to disclosed and described examples, arrangements, configurations, components, elements, apparatuses, devices, systems, methods, etc. can be made and may be desired for a specific application. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Reference throughout the specification to "various embodiments," "some embodiments," "one embodiment," "some example embodiments," "one example embodiment," or "an embodiment" means that a particular feature, structure, or characteristic described in connection with the embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

The presently disclosed embodiments are generally directed to dental tools that allow dental abutments, or other dental devices that are configured to receive a fastener, to be manipulated by a dentist. Generally, an abutment having an inner shaft is selectably insertable into a head portion of a dental tool such that at least a portion of the outer periphery of the abutment is engaged with the head portion of the dental tool. Once inserted into the grasping portion, a screw can be inserted into the inner shaft of the abutment. In some implementations, the screw can be inserted into the inner shaft of the abutment before the abutment is grasped by the dental tool. In any event, the abutment can be positioned proximate to an implant through manipulation of the dental tool by the dentist. Once positioned over the implant, the dentist can continue to hold the dental tool to maintain the relative position of the abutment with regard to the implant and thread the screw into the implant using a driver. Once the abutment is secured to the implant, the dental tool can release the abutment so that the dental tool can be removed from the mouth.

As described in more detail below, dental tools in accordance with the present disclosure can generally include a head configured to selectively retain an abutment during a dental procedure. The head can be sized such that it can easily be placed within the oral cavity. A central bore of the head portion can hold an abutment in place while affixing the abutment to an implant. The central bore can have a radius in the range of about 3 mm to about 8 mm, for example. In some embodiments, the head portion can comprise a resilient collar that defines the central bore that is dimensioned to frictionally receive an abutment. In other embodiments, the head portion can include a plurality of pivotable gripping paddles. Each of the gripping paddles can be coupled to an actuation member, such as a control cable.

The dental tool can also comprise a handle extending outwardly from the head portion. The handle can have any suitable configuration and can include, for example, gripping elements (such as grooves, knurls, or the like). Furthermore, the handle can be generally straight, curved, or have a combination of straight sections and curved sections. In some embodiments, the handle has a length in the range of about 5 cm to about 10 cm.

The dental tool can generally be a disposable or single-use tool. In other embodiments, portions of the dental tool, such as the entire head or components of the head can be replaceable. In some embodiments, the entire tool, or portions thereof, can be sterilized (i.e. via autoclaving) or disinfected in between uses. In some embodiments, a kit is provided comprising the dental tool and a plurality of replaceable and/or interchangeable components, as described in more detail below.

In some embodiments, the handle is pivotable with respect to the head. The handle can be pivotable in one axis, two axes, or a plurality of axes (i.e., via a ball joint). Facilitating the head to pivot relative to the handle can improve the dentist's ability to reach various positions within a patient's mouth. Additionally or alternatively, the handle can be selectably shapeable, such as in a "gooseneck" fashion or using a plurality of hinged links, for example, to aid the dentist in placing the dental tool within the oral cavity.

Figure 2:
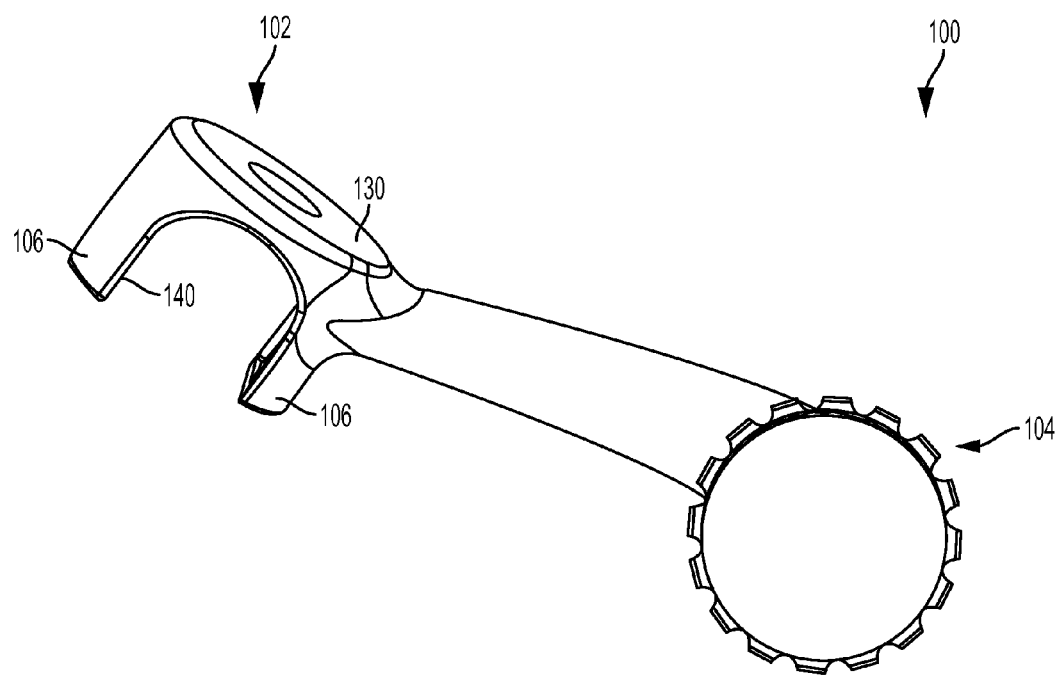
FIG. 2 is an end view taken from the proximal end of the dental tool depicted in FIG. 1.
Figure 3:
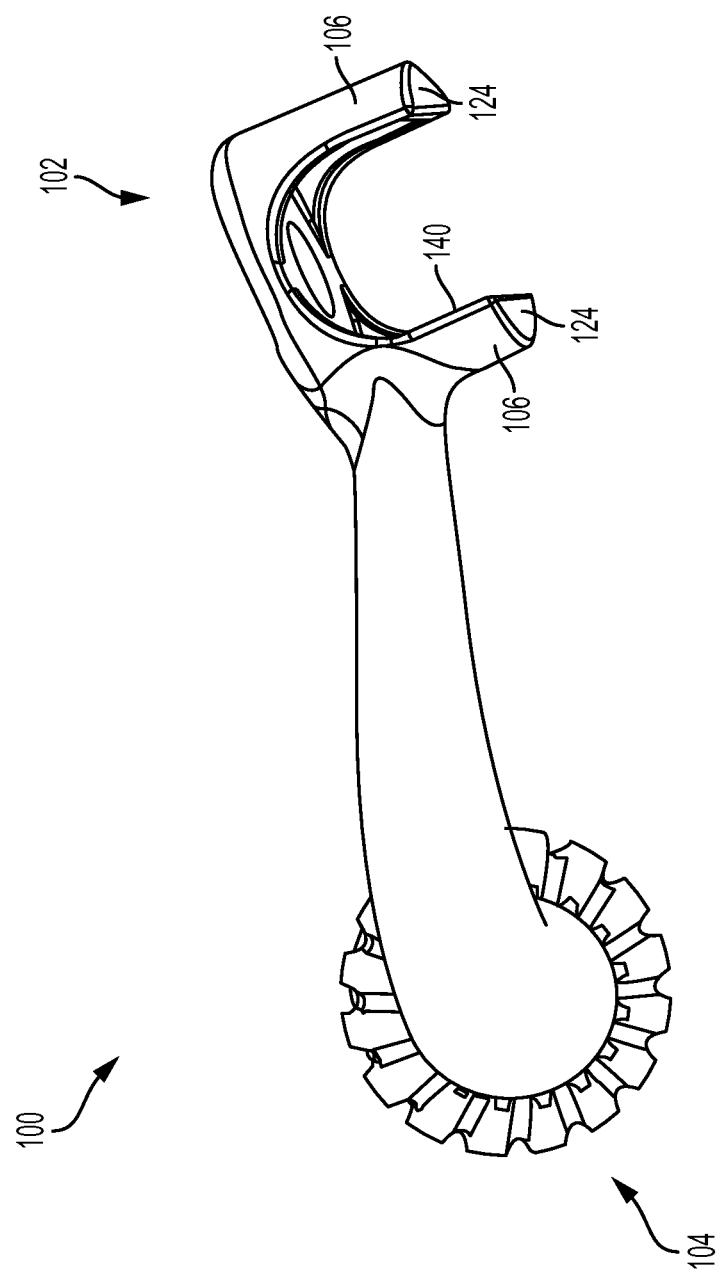
FIG. 3 is an end view taken from the distal end of the dental tool depicted in FIG. 1.
Figure 4:
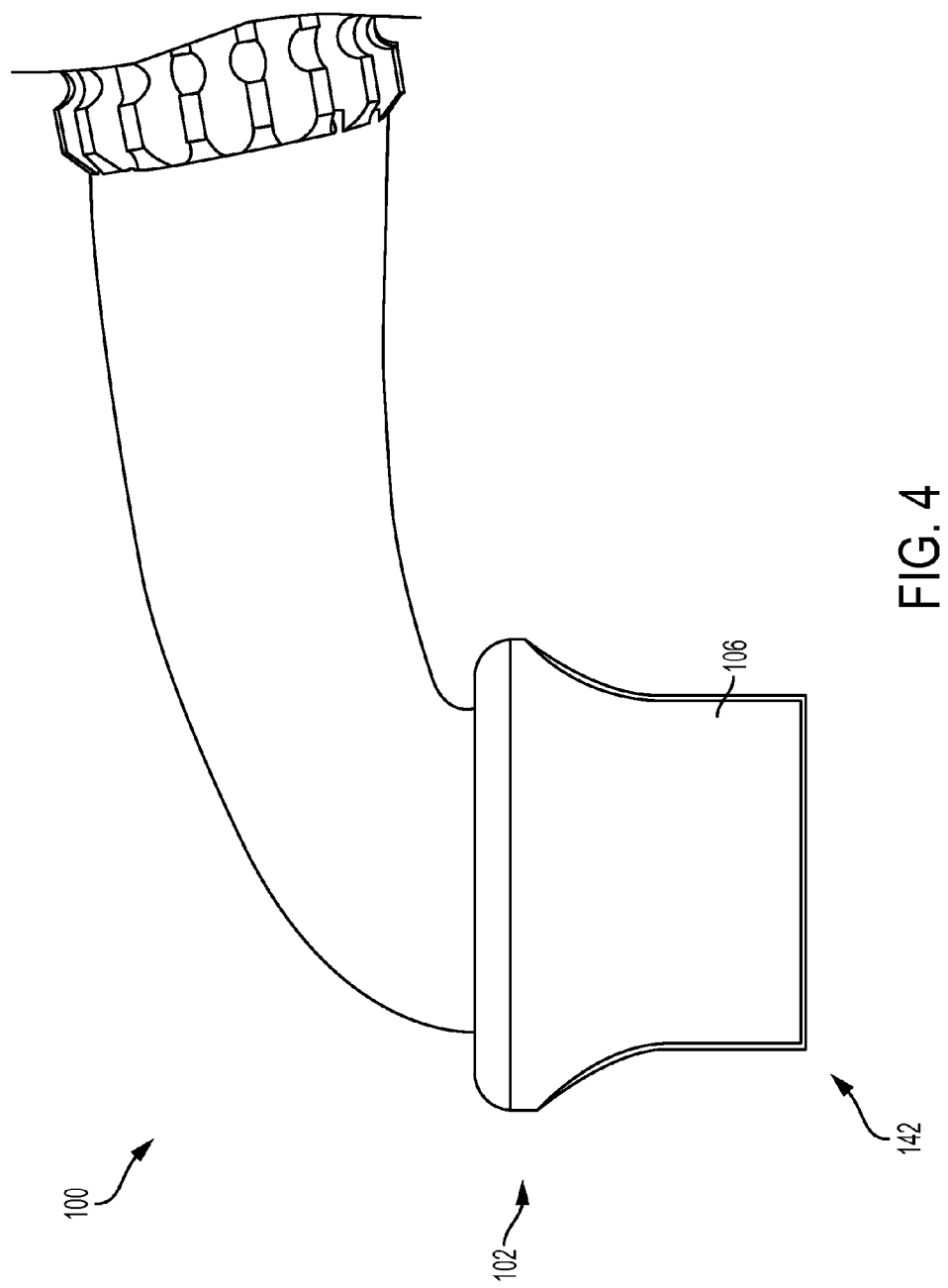
FIG. 4 is a side view of a head portion of the dental tool depicted in FIG. 1.
Figure 5:
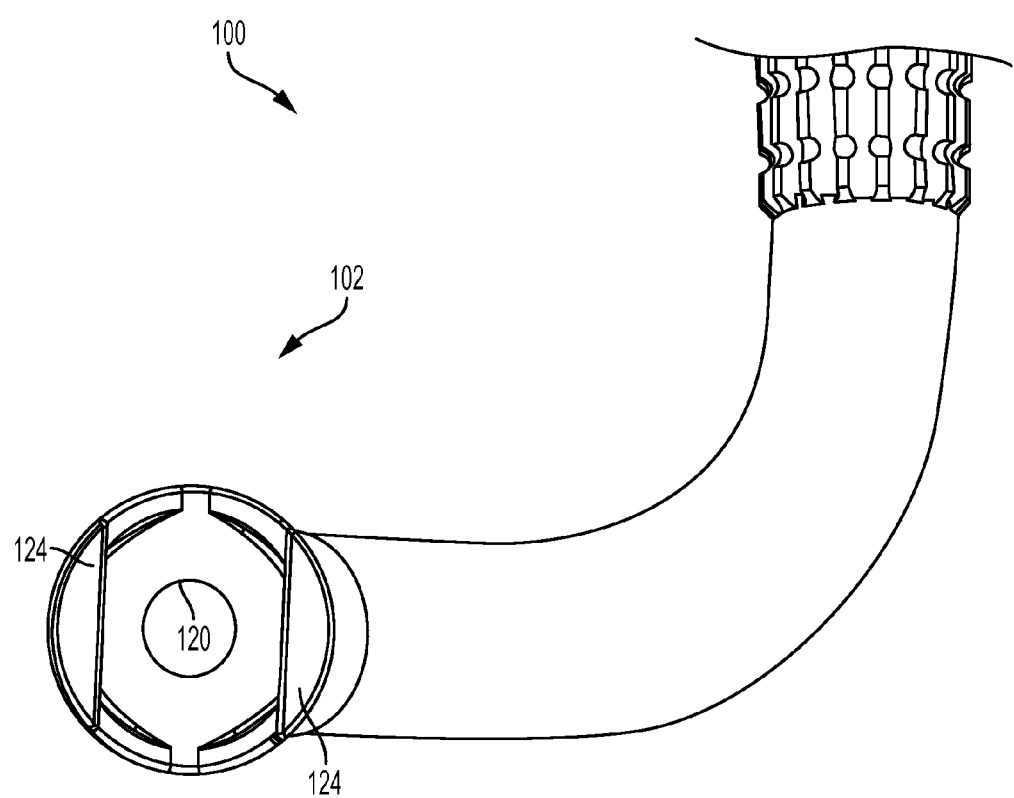
FIG. 5 is a bottom view of a head portion of the dental tool depicted in FIG. 1.
Figure 6:
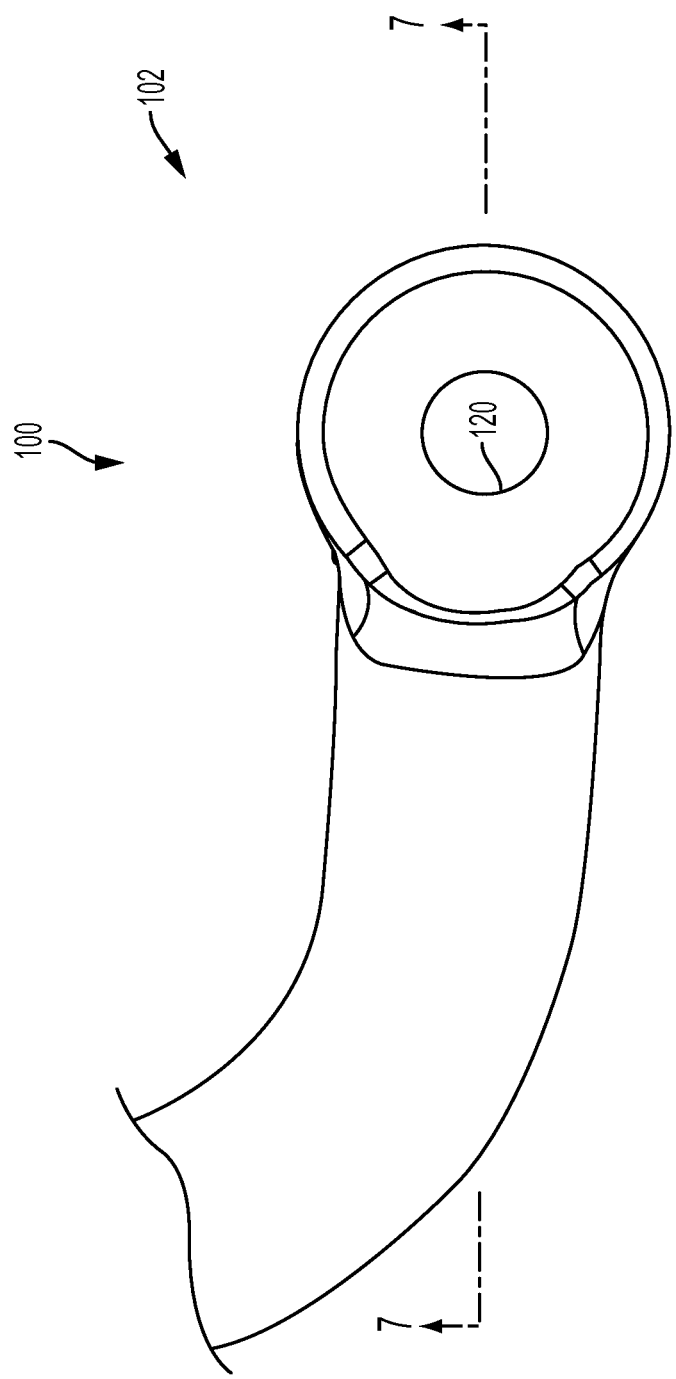
FIG. 6 is a top view of a head portion of the dental tool depicted in FIG. 1.
Figure 7:
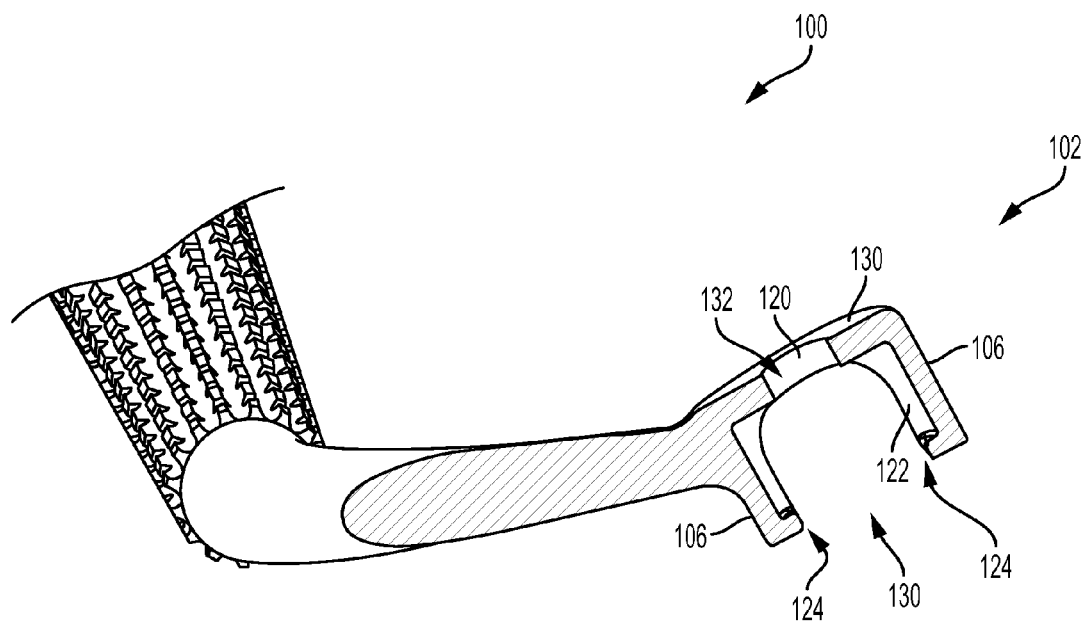
FIG. 7 is a cross-sectional view of FIG. 6 taken along line 7-7.

Referring now to FIGS. 1-7, a non-limiting example embodiment of a dental tool 100 having a head portion 102 and a handle 104 is depicted. For clarity, a resilient collar has been omitted from the head portion 102. FIG. 1 depicts a perspective view of the dental tool 100. FIG. 2 is an end view taken from the proximal end of the dental tool depicted in FIG. 1. FIG. 3 is an end view taken from the distal end of the dental tool 100 depicted in FIG. 1. FIG. 4 is a side view of the head portion 102 of the dental tool 100 depicted in FIG. 1. FIG. 5 is a bottom view of the head portion 102 of the dental tool 100 depicted in FIG. 1. FIG. 6 is a top view of the head portion 102 of the dental tool 100 depicted in FIG. 1. FIG. 7 is a cross-sectional view of FIG. 6 taken along line 7-7.

In the illustrated embodiment, the head portion 102 of the dental tool 100 has a circular sidewall 106 that has an inner surface 122 (FIG. 7). The inner surface 122 of the side wall 106 defines a head bore 122 that is in communication with a bottom opening 130 and a top opening 132 of the head portion 102. In some embodiments, the bottom opening 130 and the top opening 132 can be similarly sized, whereas in other embodiments, the top opening 132 is smaller than the bottom opening 130, as shown in FIGS. 1-7. As described in more detail below, a resilient collar can be housed within the head portion 102.

As shown in FIG. 1, the head portion 102 can be angled in a first axis relative to the handle 104, and as shown in FIG. 2. The head portion 102 can also be angled in a second axis relative to the handle 104. This angled arrangement can generally aid in the manipulation and placement of the dental tool 100 within a patient's mouth and proximate to a work site. Furthermore, while FIG. 1 shows the angle of the head portion 102 is fixed relative to the handle 104, in other embodiments, the head portion 102 can pivot, rotate, or otherwise move relative to the handle 104.

While the sidewall 106 can extend continuously around the head bore 122, in the illustrated embodiment, as shown in FIGS. 2-3, the sidewall 106 defines notches 140. The notches 140 in the depicted embodiment are positioned on either side of the head portion 102. The placement and size of the notches 140 serve to reduce the diameter of the head portion 102 at the distal end 142, as shown in FIG. 4, while still leaving enough residual sidewall 106 to firmly grasp the resilient collar (not shown). While two notches 140 are illustrated in FIGS. 1-7, other embodiments can utilize a different number of notches having any suitable shape without departing from the scope of the present disclosure. Furthermore, while the notches 140 illustrated in FIG. 1-6 extend for substantially the entire vertical length of the sidewall 106, in other embodiments, the notches can be smaller.

In some embodiments, the head portion 102 has a top surface 130 that defines a tool bore 120. The tool bore 120 can generally be coaxial with the head bore 122. As described in more detail below, the head bore 122 can be sized to receive the head of a driver.

As shown in FIGS. 3 and 5, the sidewall 106 can define a shoulder 124 that extends into the head bore 122. When a resilient collar is inserted into the head portion 102, the shoulder 124 can generally maintain placement of a resilient collar relative to the head portion 102, as shown in more detail below.

The head portion 102 and the handle 104 can be made from the same or different materials, or combination of materials. While any suitable material can be used, in some embodiments, the head portion 102 and/or the handle 104 can be made from medical grade plastics, epoxy, resins, dissolvable dental glue, rubber, silicone, rubber, silicone, and/or stainless steel.

Figure 8:
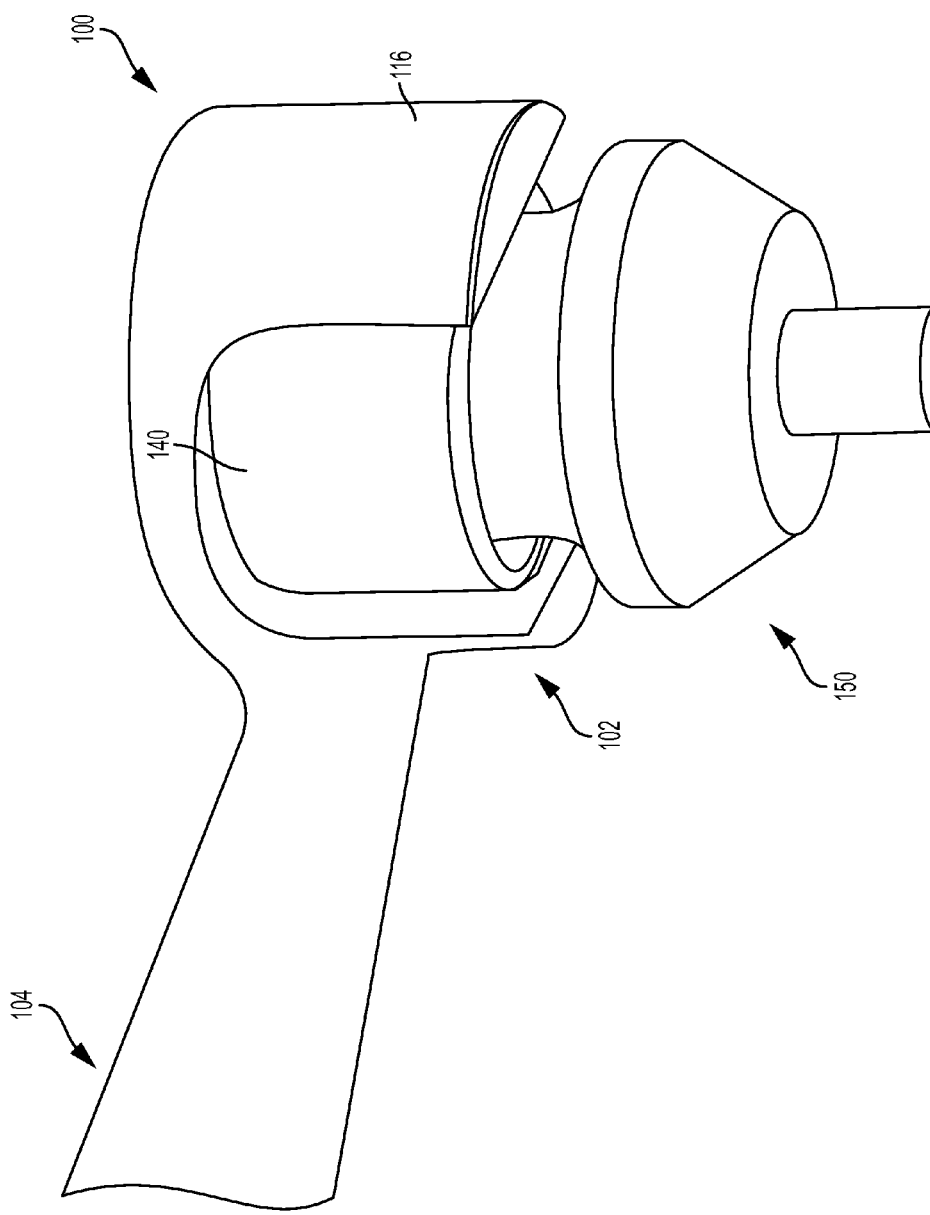
FIGS. 8-9 depict an example dental tool during operational engagement with an abutment.
Figure 9:
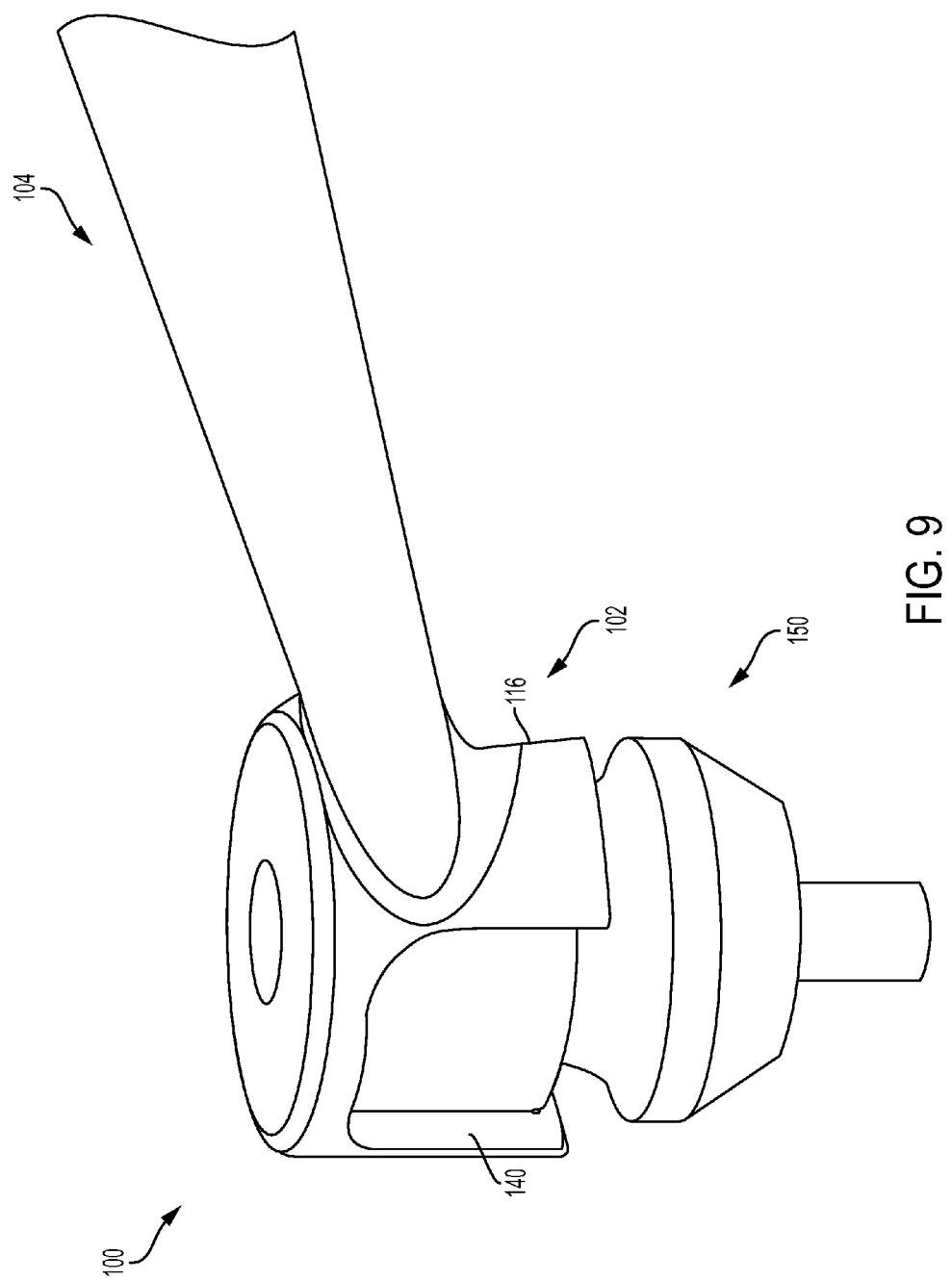
Figure 10:
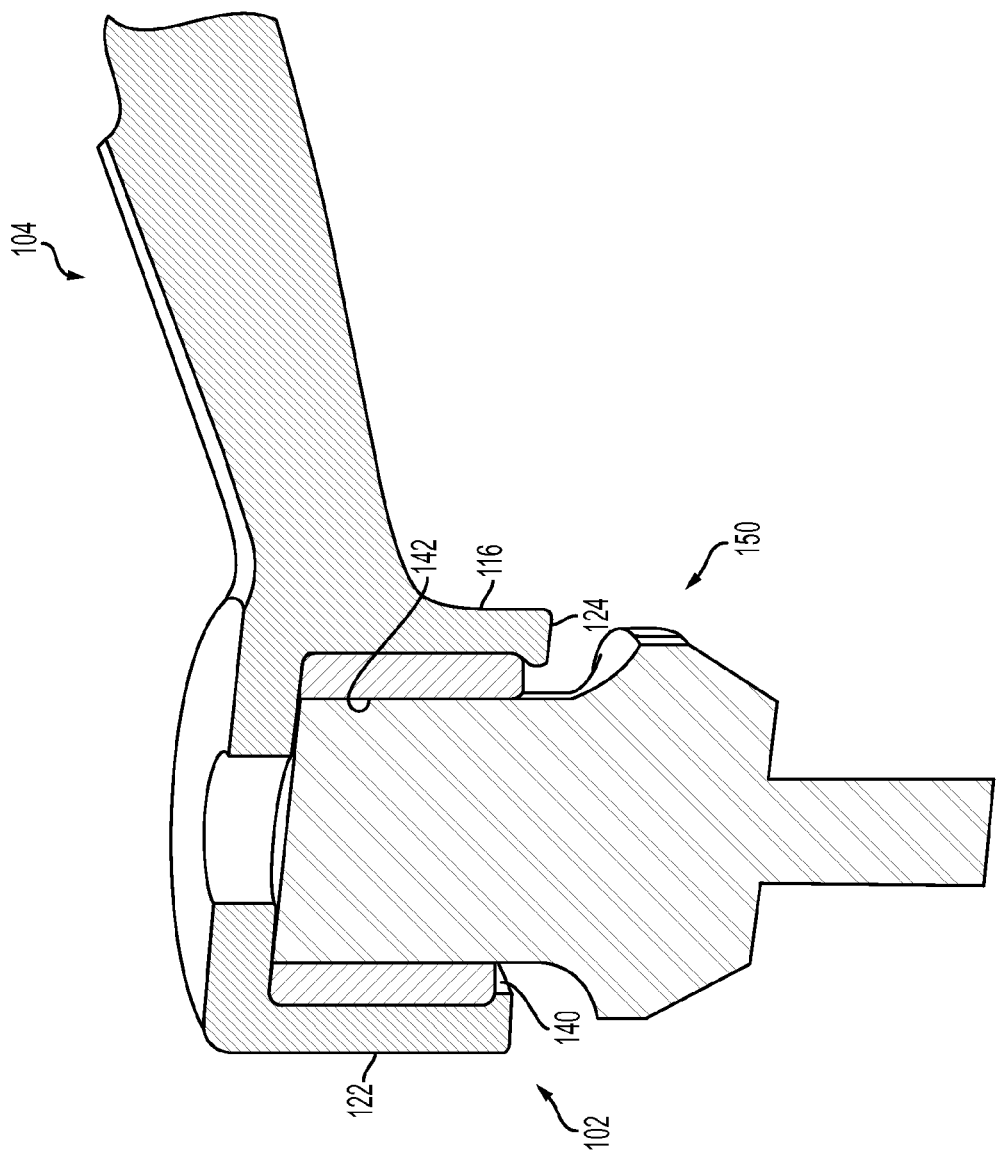
FIG. 10 depicts a cross-sectional view of the head portion as shown in FIGS. 8-9.
Figure 11:
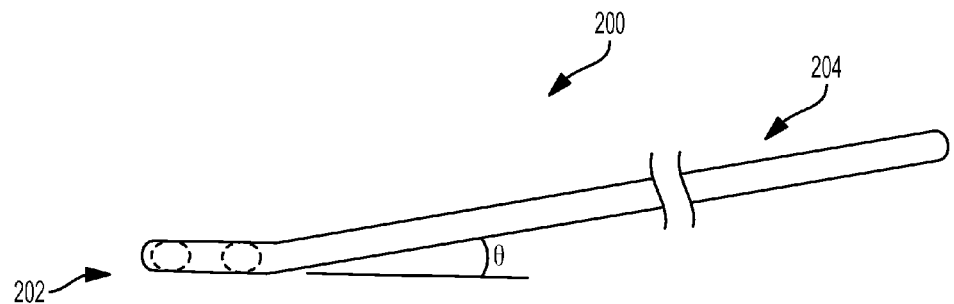
FIG. 11 depicts a side view of an example dental tool.
Figure 12:
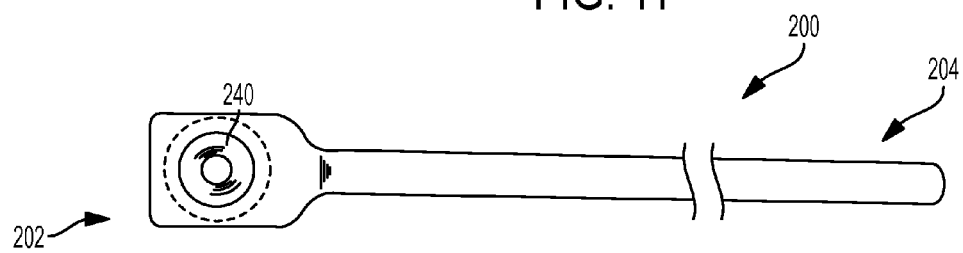
FIG. 12 depicts a top view of an example dental tool.
Figure 13:
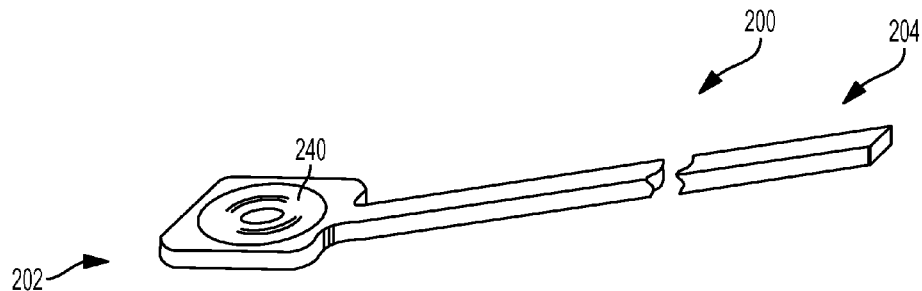
FIG. 13 depicts a perspective view of an example dental tool.

FIGS. 8-10 depict the dental tool 100 during operational engagement with an abutment 150. FIGS. 8 and 9 depict perspective views and FIG. 10 depicts a cross-sectional view of the head portion 102 as shown in FIGS. 8-9. In the illustrated embodiment, a resilient collar 140 is shown being housed in the head bore 122. While the resilient collar 140 is depicted as being cylindrically shaped, this disclosure is not so limited. The resilient collar 140 can be any suitable shape or configuration, such as an O-ring, gasket, or other suitable grasping structure having an opening for receiving an abutment. In any event, the opening defined by the resilient collar 140 can be referred to as a central bore 142. An abutment 150 is shown being held within the central bore 142 through frictional engagement with the resilient collar 140. As is to be appreciated, once the abutment 150 is engaged with the resilient collar 140 a dentist can transport the abutment 150 to the desired location within a patient's mouth to affix the abutment 150 to an implant.

Figure 14:
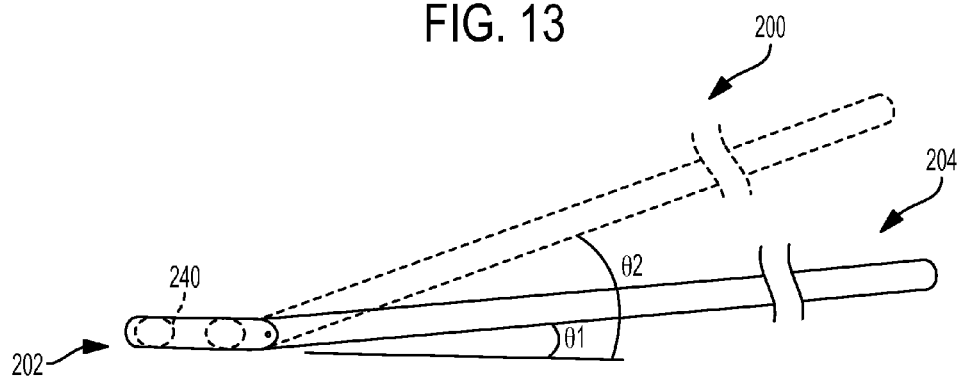
FIG. 14 depicts a side view of an example hinged dental tool.
Figure 15:
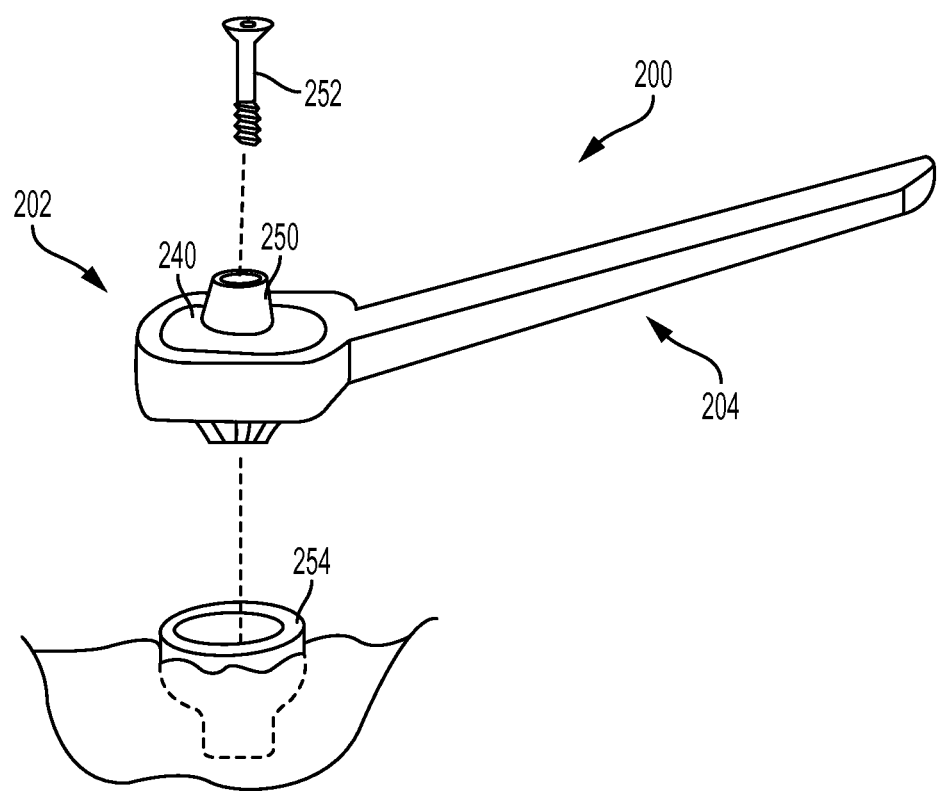
FIG. 15 is an exploded view schematically depicting an example dental tool grasping an abutment to aid in the driving of the screw into an implant.
Figure 16A:
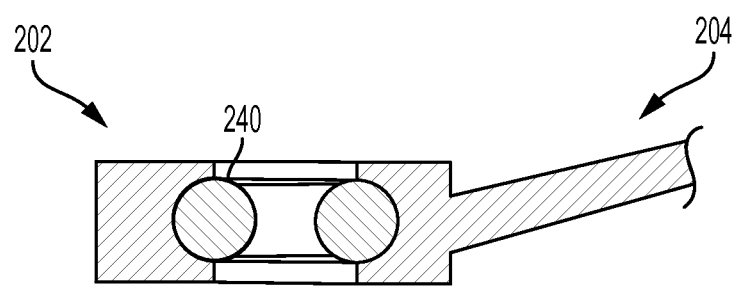
FIGS. 16A-16B depict a cross-sectional view of a head portion of an example dental tool with an abutment shown engaged with the resilient collar in FIG. 16B.
Figure 16B:
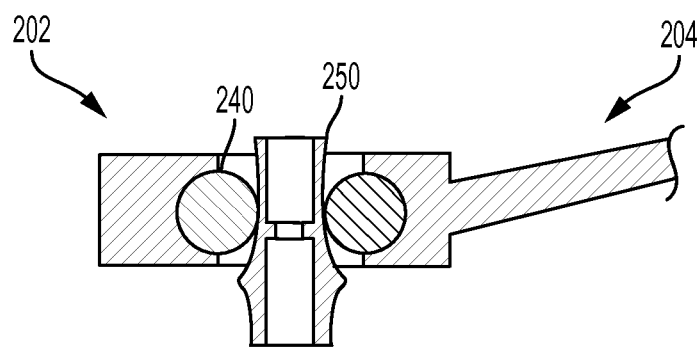

Dental tools in accordance with the present disclosure can have a variety of arrangements and configurations, some of which are depicted herein. FIGS. 11-14, for example, depict a dental tool 200 in accordance with another non-limiting embodiment. The dental tool 200 is depicted having a head portion 202 and a handle 204. The head portion 202 houses a resilient collar 240. In this embodiment, the resilient collar 240 is shown as an O-ring. As shown in FIG. 14, the handle 204 can be hinged such the angle between the head portion 202 and the handle 204 can be selected by a user. In some embodiments, as shown in FIG. 1, the angle of a head portion to a handle can be fixed such that it is configured to access a certain side of a patient's mouth. In some embodiments, the head portion can be selectively attachable to the handle (i.e., through a threaded engagement, a friction fit engagement, a snap fit, a magnetic engagement, etc.). FIG. 15 is an exploded view schematically depicting the dental tool 200 grasping an abutment 250 to aid in the driving of the screw 252 into an implant 254. FIGS. 16A-16B depict a cross-sectional view of the head portion 202, which the abutment 250 shown engaged with the resilient collar 240 in FIG. 16B.

In accordance with some embodiments, the resilient collar can be a conventional O-ring, while in other embodiments the resilient collar can have a specific profile that is configured to aid in the handling of abutments. The resilient collar can generally define a central bore for receiving abutments. The size of the central bore is typically slightly smaller than the outer dimension of an abutment to allow for frictional engagement between the inner surface of the resilient collar and the outer surface of the abutment. The central bore can be circular, star-shaped, or have any other suitable shape. In some embodiments, the resilient collar can include various elements configured to aid in gripping an abutment. For example, a resilient collar can comprise one or more inner ribs or knobs protruding inwardly, that are vertically or horizontally arranged, that can assist with gripping various abutments. The resilient collar can be made from any suitable material, such as an elastomeric material or other material providing a desired level of viscoelasticity to frictionally engage an abutment. The resilient collar can be, in some embodiments, made from silicone, a medical grade silicone, or rubber, for example.

Furthermore, an outer surface of the resilient collar can also be configured to aid in the permanent or selective attachment of the resilient collar to the head of the dental tool. For example, the resilient collar can comprise detents or other structural elements that mate with corresponding elements of the head portion. In one embodiment, the resilient collar comprises a rim protruding from a bottom surface. The head comprises a corresponding notch that is sized to receive the rim. The rim of the resilient collar can be inserted into the notch for selective attachment of the resilient collar to the head. In some embodiments, the rim can comprise a distal flare to mate with a corresponding flare within the notch.

Figure 17A:
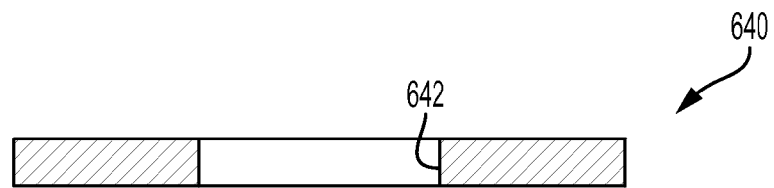
FIG. 17A depicts a cross-sectional view of an example resilient collar.
Figure 17B:
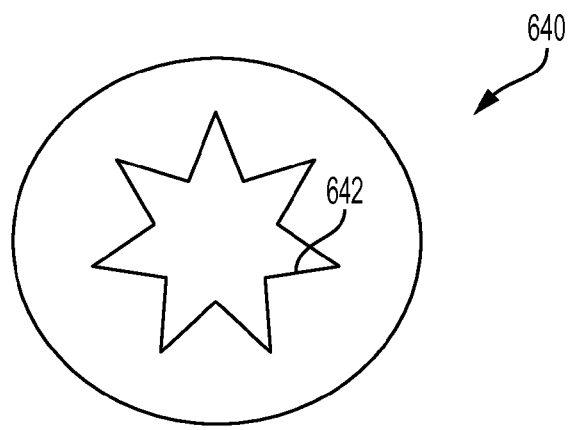
FIG. 17B depicts a top view of the resilient collar of FIG. 17A.
Figure 18:
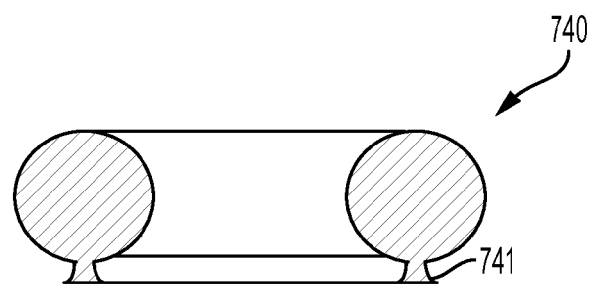
FIG. 18-21 depict cross-sectional views of example resilient collars.
Figure 19:
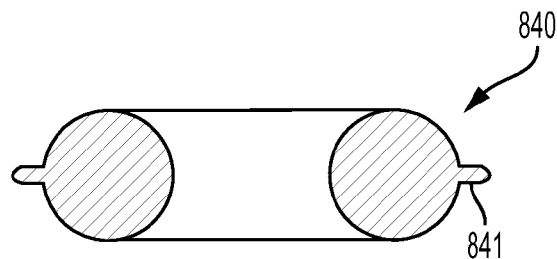
Figure 20:
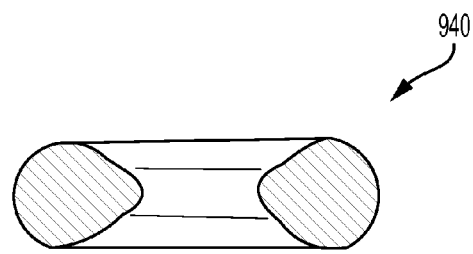
Figure 21:
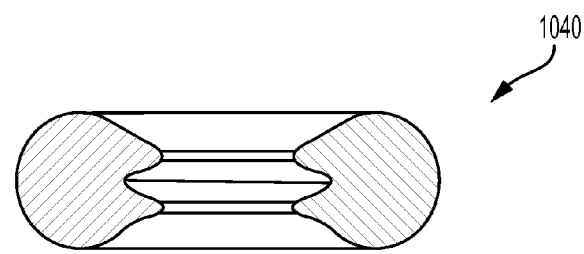

FIGS. 17A-17B and 18-21 depict example resilient collar configurations in accordance with various non-limiting embodiments that can be used with various styles of dental tools in accordance with the present disclosure. FIG. 17A depicts a cross sectional view of a resilient collar 640 and FIG. 17B shows a top view of the resilient collar 640. The resilient collar 640 defines a central bore 642 that is star-shaped. FIG. 18 depicts an example resilient collar 740 comprising an annular rib 741 extending downward. FIG. 19 depicts an example resilient collar 840 comprising an annular rib 841 extending outward. FIG. 20 depicts an example resilient collar 940 that has a tear drop cross-sectional profile, while FIG. 21 depicts a resilient collar 1040 having a double tear drop cross-sectional profile.

Figure 22:
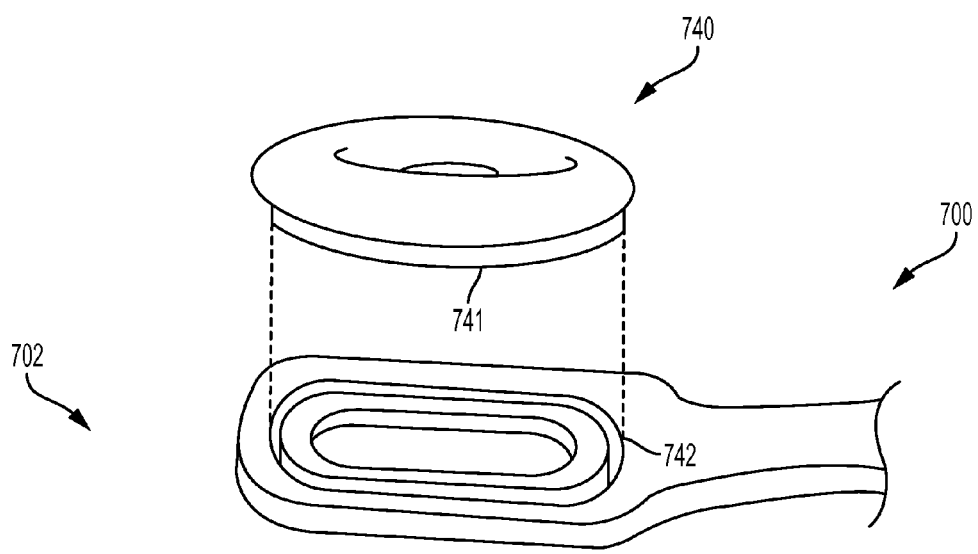
FIG. 22 is an exploded view of an example resilient collar having an annular rib and an example dental tool.
Figure 23:
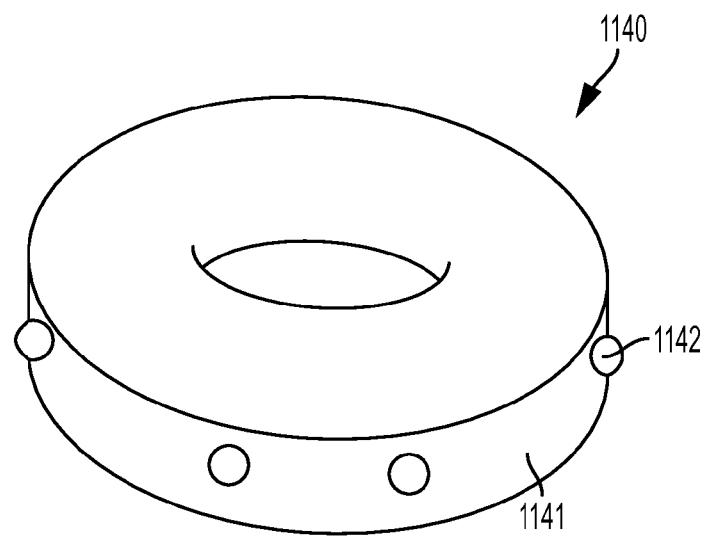
FIG. 23 depicts a resilient collar comprising a rib extending downwardly and a plurality of extensions extending outwardly from the rib.
Figure 24:
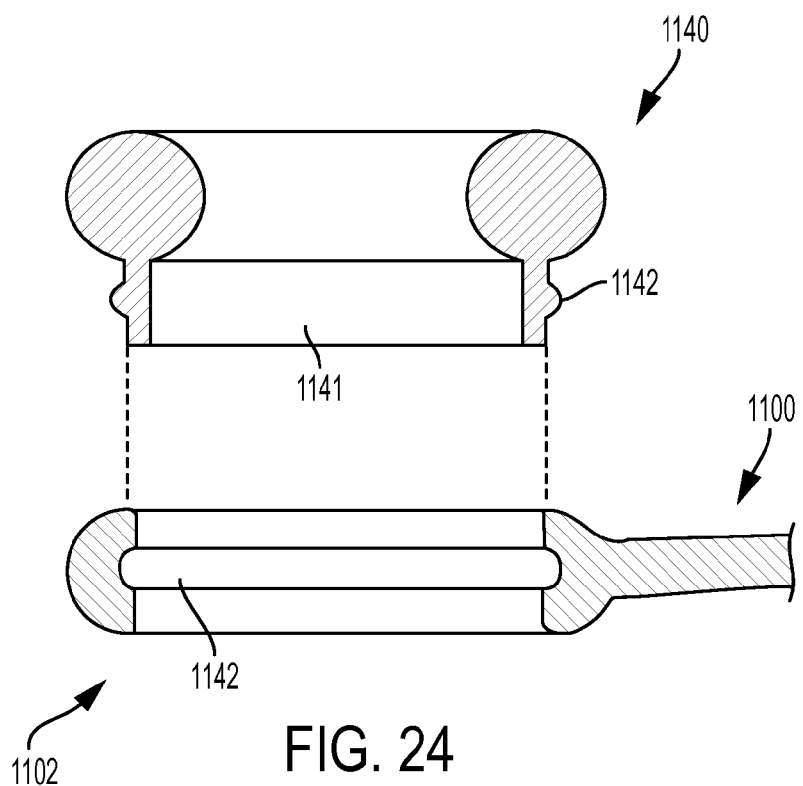
FIG. 24 is an exploded view of the resilient collar of FIG. 23 being received into an example dental tool.

In accordance with various embodiments, the resilient collar can be selectively removed from the head portion of the dental tool. For instance, the resilient collar can be replaced after each use, or otherwise removable for cleaning purposes. A variety of techniques can be utilized for selective removal of the resilient collar. For example, referring to the dental tool depicted in FIGS. 8-10, the resilient collar 140 can be manually pulled from the head bore 122, such as by disengaging the resilient collar 140 with the shoulder 124 through manual manipulation. FIGS. 22-26 depict additional configurations for selectively coupling a resilient collar to a head portion in accordance with various non-limiting embodiments. In FIG. 22, for example, the annular rib 741 of the resilient collar 740 of FIG. 18 is shown being inserted into a grove 742 defined by a head portion 702 of a dental tool 700. FIG. 23 depicts a resilient collar 1140 comprising a rib 1141 extending downwardly. A plurality of extensions 1142 extend outwardly from the rib 1141. As shown in FIG. 24, the extensions 1142 can extend into a cavity 1142 defined by a head portion 1102 allowing a user to insert and remove the resilient collar 1140 from the cavity 1142.

Figure 25:
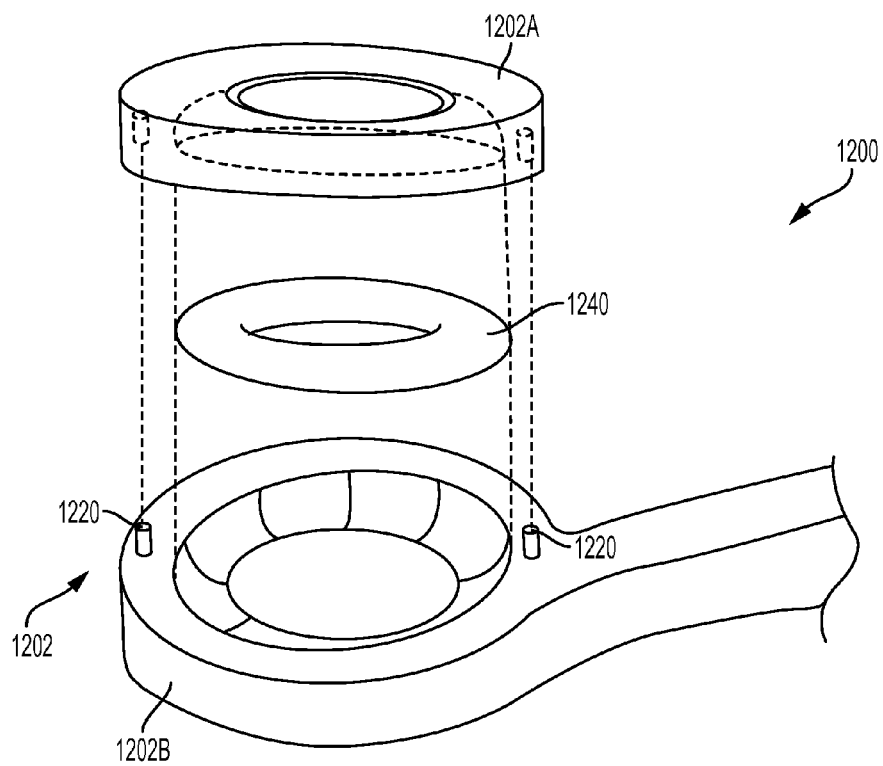
FIG. 25 is an exploded view of an example dental tool having a head portion that includes a top piece that can be separated from a bottom piece.
Figure 26:
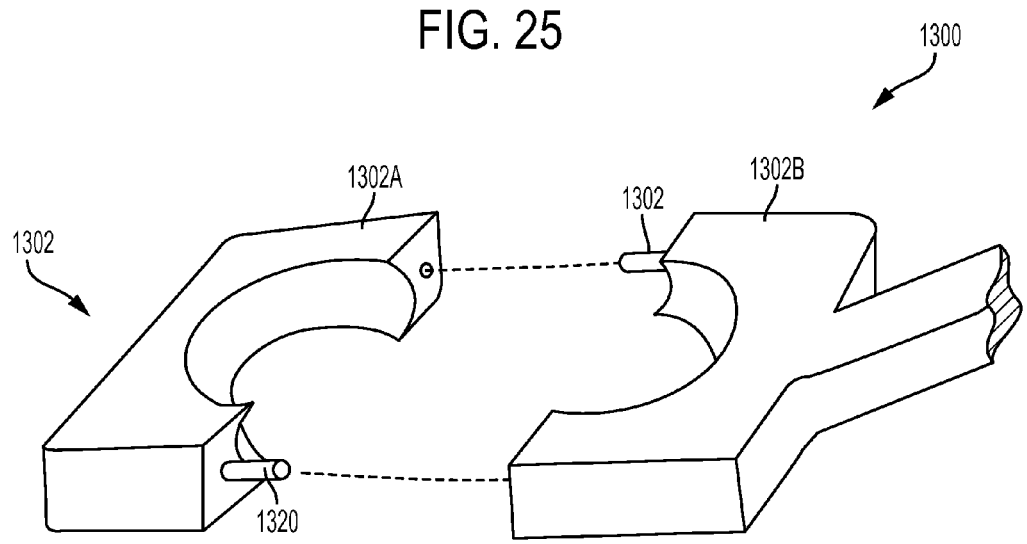
FIG. 26 is an exploded view of an example dental tool having a head portion that includes an end piece that can be separated from a base piece.

In accordance with various embodiments, the head of the dental tool can comprise a plurality of mating pieces. When the mating pieces are separated, a resilient collar can be inserted and then the mating pieces can be brought together to secure the resilient collar in place. In some embodiments, the head portion is a unitary piece with a sidewall defining a shoulder for selectively retaining a resilient collar within the head portion. FIG. 25 depicts an example dental tool 1200 having a head portion 1202 that includes a top piece 1202A that can be separated from a bottom piece 1202B. Once separated, a resilient collar 1240 can be placed in a cavity defined by the bottom piece 1202B and the top piece 1202A can be re-connected to the bottom piece 1202B. While alignment posts 1220 are illustrated in FIG. 25, other suitable connection techniques can be used. FIG. 26 depicts an example dental tool 1300 having a head portion 1302. The head portion 1202 includes an end piece 1302A that can be separated from the base piece 1302B. Once separated, a resilient collar (not shown) can be placed in a cavity defined by the base piece 1302B and the end piece 1302A can be re-connected to the base piece 1302B. While alignment posts 1220, 1320 are illustrated in FIGS. 25-26, other suitable connection techniques can be used, such as magnetic attachment, clips, and so forth.

Figure 27:
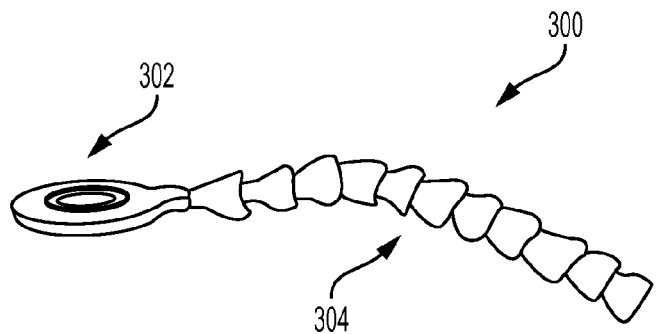
FIG. 27 depicts another example dental tool having interconnected segments.
Figure 28:
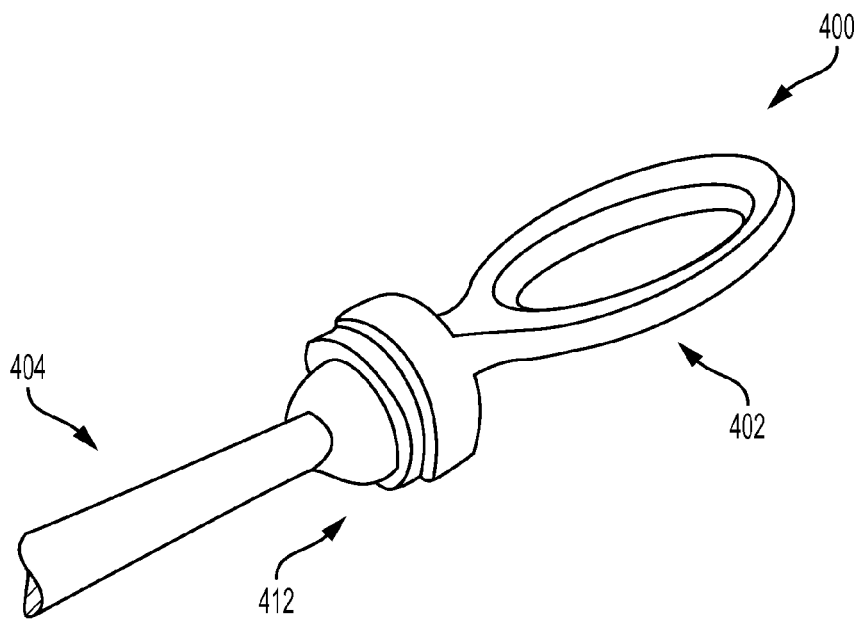
FIG. 28 depicts another example dental tool having a ball joint.
Figure 29:
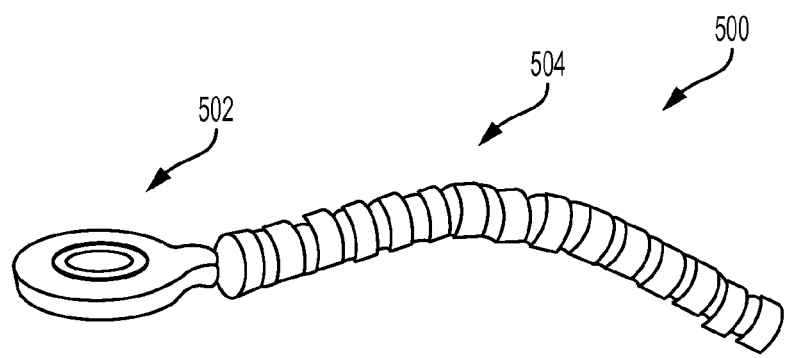
FIG. 29 depicts another example dental tool having interconnected segments.

FIGS. 27-29 depict additional non-limiting examples of dental tools in accordance with the present disclosure. The dental tool 300 depicted in FIG. 27 and the dental tool 500 depicted in FIG. 29 are examples of gooseneck style tools. In both embodiments, the desired position of head portion (302, 502) can be set by the use through manipulation of interlocking segments along the handle (304, 504). The dental tool 400 in FIG. 28, shown without a resilient collar, utilizes a ball joint 412 that connects the head portion 402 to the handle 404. The ball joint 412 can allow the user to position the head portion 402 in a variety of positions relative to the handle 404.

Figure 30A:
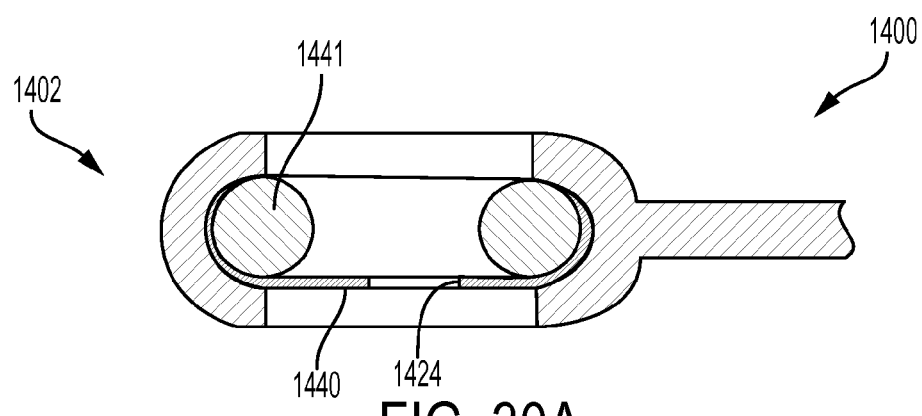
FIGS. 30A-30B depict cross-sectional views of a dental tool comprising an elastomeric sheet.
Figure 30B:
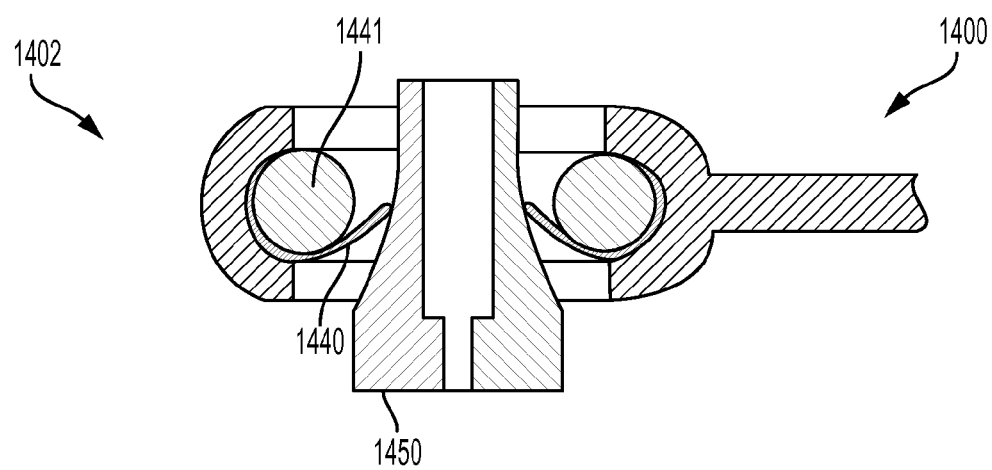
Figure 31:
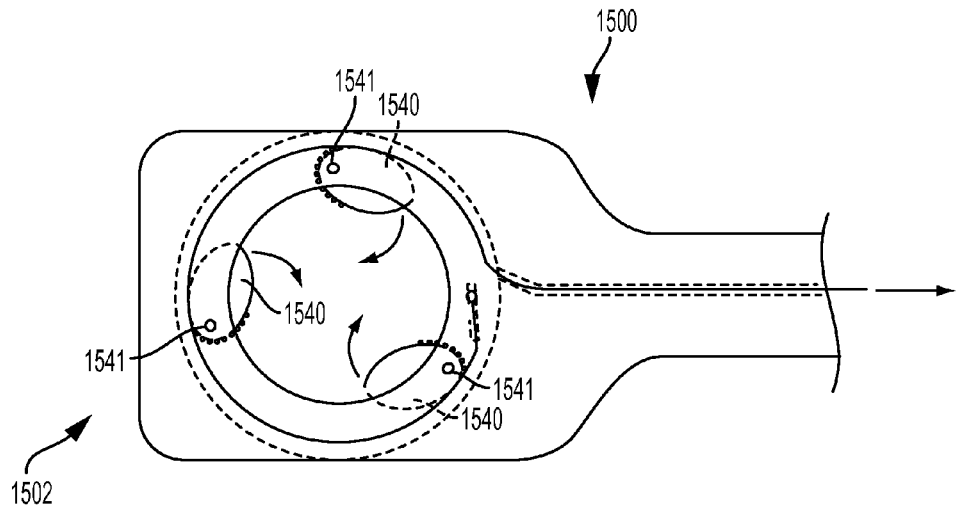
FIGS. 31-32 depict an example dental tool comprising pivotable gripping paddles.
Figure 32:
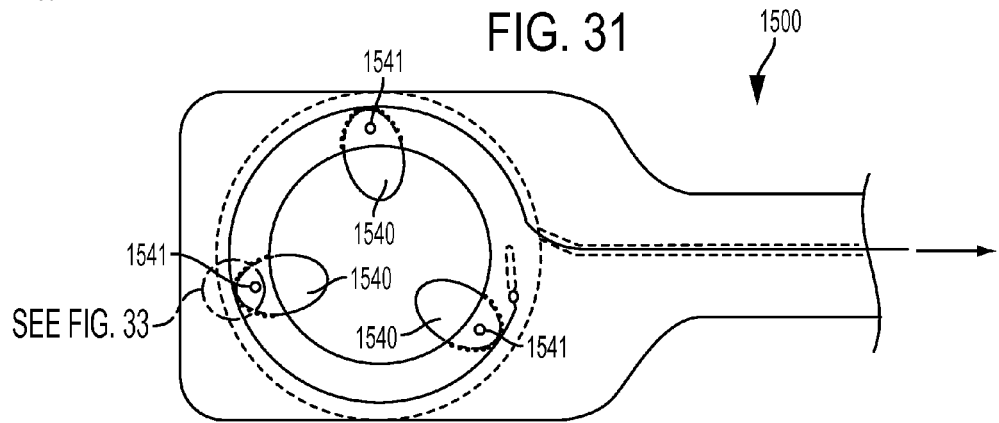
Figure 33:
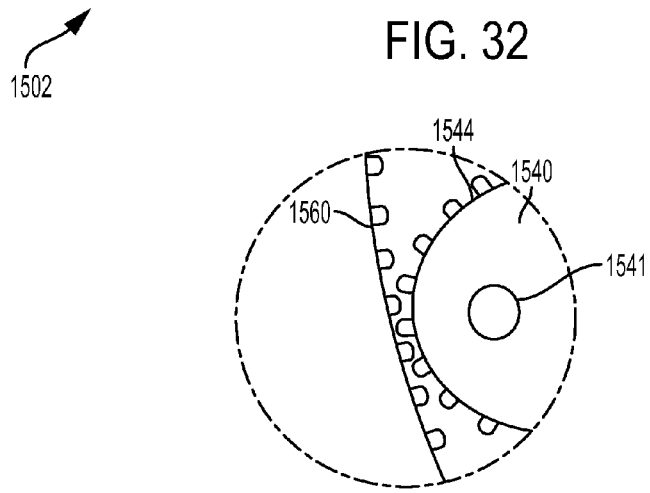
FIG. 33 is an enlarged view of a portion of FIG. 32.

In some embodiments, a dental tool comprises an elastomeric sheet defining a central bore, with the elastomeric sheet spanning a head bore defined by a sidewall. FIGS. 30A-30B depict a cross-sectional view of a dental tool 1400 comprising an elastomeric sheet 1440. The elastomeric sheet 1440 can have one or more layers of material. A reinforcing layer can be used proximate the aperture to maintain the desired tension. When the dentist places the head portion 1402 of the dental tool 1400 over an abutment 1450 (i.e., an abutment positioned in a storage rack) and forces the head portion 1402 over the abutment 1450, the aperture of the elastomeric sheet 1440 expands to confirm to and grip the outer surface of the abutment. The position of the elastomeric sheet 1440 relative to the head can be maintained by an O-ring 1441 engaged with the head portion 1402, with outer portions of the elastomeric sheet 1440 sandwiched between the outer surface of the O-ring 1441 and the inner surface of a head bore 1422 defined by the head portion 1440. The elastomeric sheet 1440 can be made from any suitable material, such as silicone or latex, for example. The elastomeric sheet can have any suitable shape, such as circular, square, and so forth.

Figure 37:
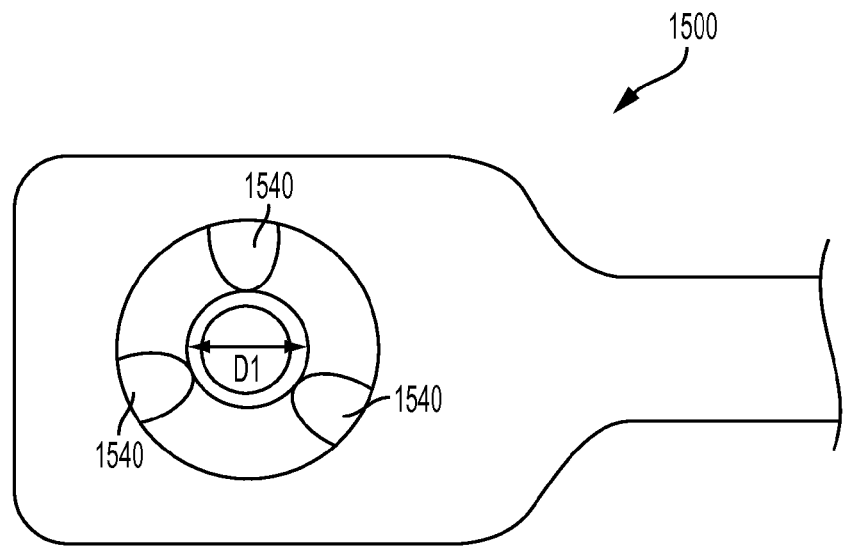
FIGS. 37-38 depict an example dental tool comprising pivotable gripping paddles.
Figure 38:
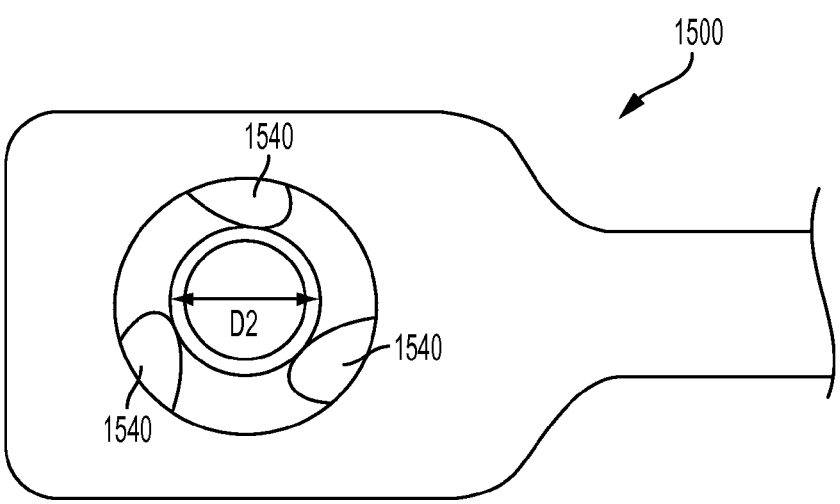

The head portion of the dental tool can additionally or alternatively comprises a plurality of pivotable gripping paddles, as illustrated by the pivotable gripping paddles 1540 of dental tool 1500 schematically depicted in FIGS. 31-38. Each of pivotable gripping paddles 1540 can be selectively moveable between a first position (FIG. 31) and a second position (FIG. 32), with each pivotable gripping paddle 1540 pivoting about a respective pivot 1541. The pivotable gripping paddles 1540 can be collectively moved from the first position (FIG. 31) to the second position (FIG. 32) to grip the outer surface of an abutment. As shown in FIG. 37 and FIG. 38, a variety of differently sized abutments can be gripped. In some embodiments, the pivotable gripping paddles 1540 are biased to the second position (i.e. the gripping position) while in the other embodiments the pivotable gripping paddles are biased to the first position (i.e. the releasing position). The pivotable gripping paddles 1540 can be made from any suitable material, such as silicone, ceramics, or metals, for example.

Figure 34:
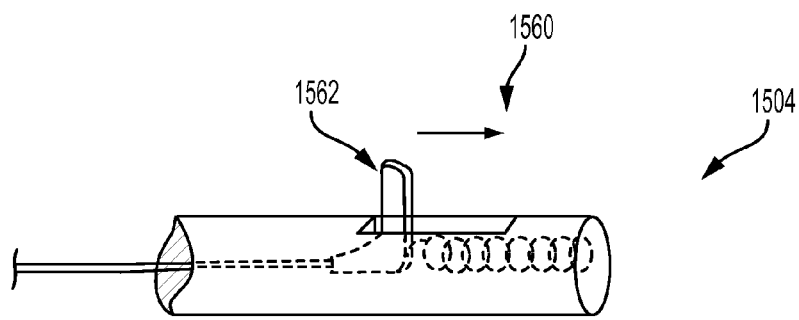
FIG. 34 depicts a proximal end of an example dental tool.
Figure 35:
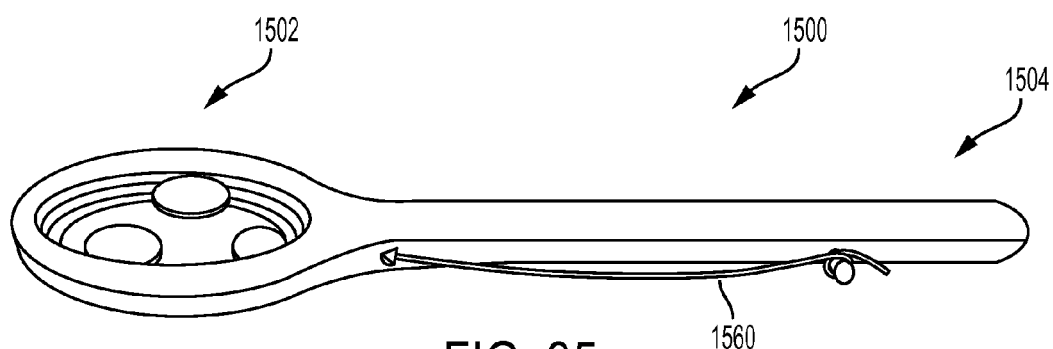
FIG. 35 depicts an example dental tool.
Figure 36:
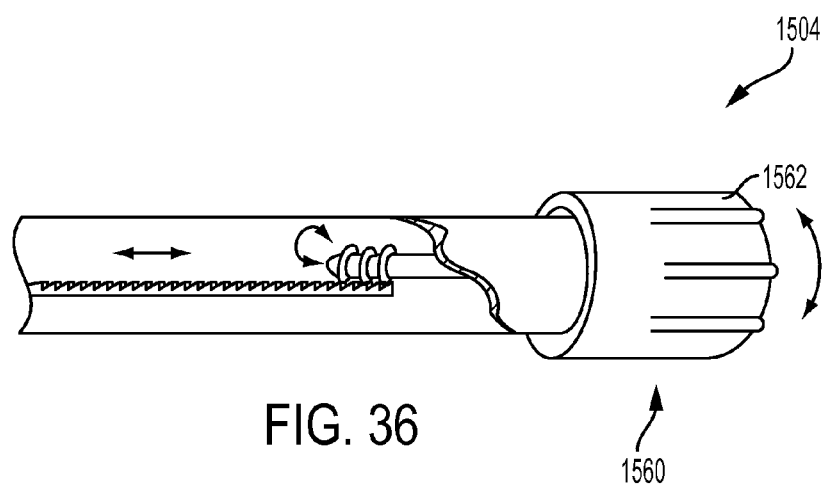
FIG. 36 depicts a proximal end of an example dental tool.

Each of the pivotable gripping paddles 1540 can be coupled to an actuation member, where proximal and distal movement of the actuation member 1560 causes the pivotable gripping paddles 1540 to move from one of the first and second positions to the other of the first and second positions. In some embodiments, as shown in FIG. 34, the actuation member 1560 can be routed internally through the handle and coupled to a trigger assembly positioned 1562 at the proximal end of the handle. The trigger assembly can comprise, for example, a control level (FIG. 34) or dial/worm gear (FIG. 36) that can be manipulated by the dentist to cause the pivotable gripping paddles 1560 to pivot.

In one embodiment, the pivotable gripping paddles 1540 have a toothed outer surface 1544 (FIG. 33), with the teeth of the toothed outer surface sized to engage teeth on the actuation member 1560. As the actuation member is drawn past the pivotable gripping paddles 1540, the interacting teeth cause the pivotable gripping paddles 1540 to rotate about their respective pivot points 1541.

Figure 39:
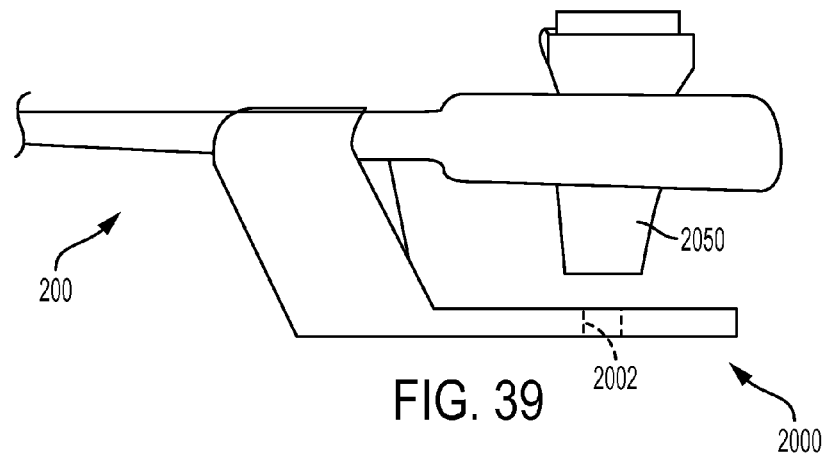
FIGS. 39-41 depict an example screw guards in accordance with various non-limiting embodiments.
Figure 40:
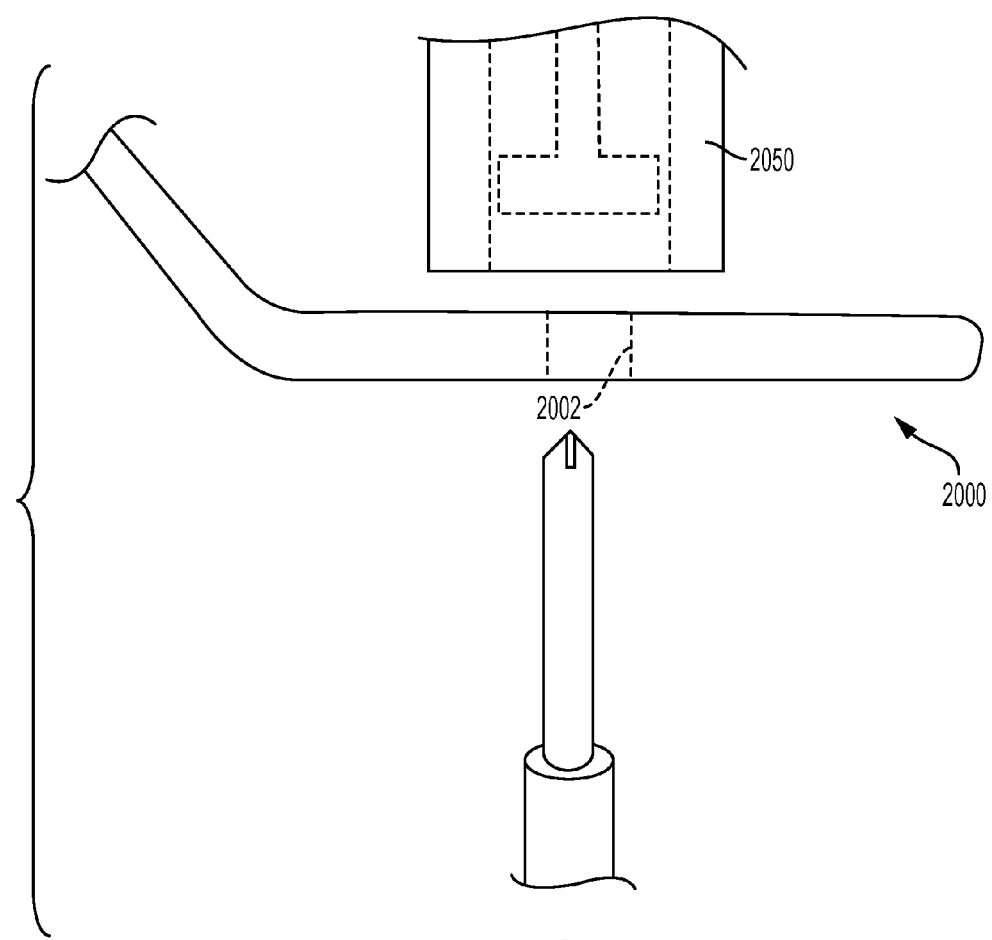
Figure 41:
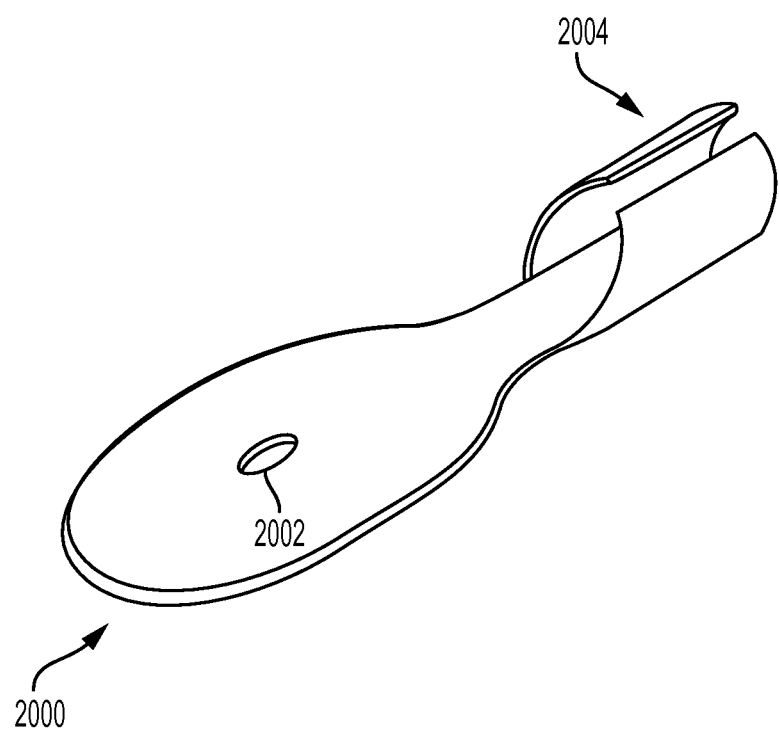

Referring now to FIGS. 39-41, in accordance with various embodiments, a dental tool can also comprise a screw guard 2000 to aid in the retention of the screw in the inner shaft of the abutment 2050 before the screw is threaded into the implant. A screw guard 2000 may be particular useful when the tool is being used to attach an abutment 2050 to an implant in the upper jaw, as gravitational forces will draw the screw out of the abutment 2050. Although it may be desirable to use the screw guard 2000 in attaching abutments to implants in the lower jaw as well in order to reduce the risk of the patient aspirating the screw. A screw guard 2000 in accordance with the present disclosure is shown in combination with an example dental tool 200, can define an aperture 2002 that is sized to be larger than the head of a driver (i.e., a screw driver or other dental driver), while be larger than the head of the screw. In this regard, the driver can be fed through the aperture 2002, but the head of the screw itself can not fit through the aperture. In some embodiments, the screw guard 2000 can be selectively attachable to a dental tool. In some embodiments, the screw guard comprises a clip 2004 (FIG. 41) that can be clipped to the handle. In other embodiments, the screw guard 2000 is integral with the dental tool. Once the screw is placed into the abutment, but before the abutment 2050 is placed in the patient's mouth, the screw guard 2000 can positioned proximate the central opening of abutment to keep the screw from falling out of the abutment. The dentist can then direct the abutment 2050 into the patient's mouth, and invert the tool if necessary, without the screw falling out of the abutment 2050. The dentist can then direct a driver through the aperture 2002 of the screw guard 2000 to access the head of the screw.

Dental tools in accordance with the present disclosure can be provided in "kit form." For example, a kit may comprise a handle and a plurality of interchangeable heads. Additionally or alternatively, the kit may comprise a plurality of replacement portions for the heads, such as a plurality of resilient collars and/or elastomeric sheets. Some kits can also include abutments. Some embodiments may include a plurality of different types of heads, such as one or more heads utilizing a resilient collar and one or more heads utilizing pivotable gripping paddles. In some embodiments, a kit can include first head portion that is angled to the right and a second head portion that is angled to the left. Depending on the location of the work area in the patient's mount, the user can attach the head portion having the desired angle to the handle.

In various embodiments disclosed herein, a single component may be replaced by multiple components and multiple components may be replaced by a single component to perform a given function or functions. Except where such substitution would not be operative, such substitution is within the intended scope of the embodiments. While various embodiments have been described herein, it should be apparent that various modifications, alterations, and adaptations to those embodiments may occur to persons skilled in the art with attainment of at least some of the advantages. The disclosed embodiments are therefore intended to include all such modifications, alterations, and adaptations without departing from the scope of the embodiments as set forth herein.

We claim:

1. A dental tool, comprising:
    A head portion, wherein the head portion comprises
        a sidewall defining an inner surface,
            wherein the inner surface at least partially defines a head bore; and
    A resilient collar, wherein the resilient collar is received into the head bore and contacts the inner surface, wherein the resilient collar defines a central bore.

2. The dental tool of claim 1, wherein the central bore is generally circular-shaped.

3. The dental tool of claim 2, wherein the central bore has a radius in the range of about 3 mm to about 8 mm.

4. The dental tool of claim 1, further comprising a handle coupled to and extending from the head portion.

5. The dental tool of claim 4, wherein the handle and head portion are formed together in a unitary one-piece construction.

6. The dental tool of claim 4, wherein the head portion is angled with respect to the handle.

7. The dental tool of claim 6, wherein the head portion is pivotable with respect to the handle.

8. The dental tool of claim 7, wherein the head portion is pivotable with respect to the handle in a plurality of axes.

9. The dental tool of claim 4, wherein the handle is an elongate handle extending from the sidewall.

10. The dental tool of claim 1, wherein the sidewall has a proximal end and a distal end, and wherein the distal end defines a shoulder extending into the head bore.

11. The dental tool of claim 10, wherein the resilient collar has a proximal end and a distal end, and wherein the resilient collar is engaged with the shoulder to maintain placement of resilient collar relative to the head portion.

12. The dental tool of claim 1, wherein the sidewall defines a first sidewall notch.

13. The dental tool of claim 12, wherein the sidewall defines a second sidewall notch positioned opposite of the first sidewall notch.

14. The dental tool of claim 1, wherein the head portion comprises a top surface defining a tool bore, wherein the tool bore is axially aligned with the head bore and the central bore.

15. The dental tool of claim 14, wherein a radius of the tool bore is less than a radius of the central bore, wherein the radius of the central bore is less than a radius of the head bore.

16. The dental tool of claim 15, wherein a radius of the central bore is sized to frictionally receive a dental abutment.

17. The dental tool of claim 1, wherein the resilient collar is an O-ring.

18. The dental tool of claim 1, wherein the resilient collar is an elastomeric material.

19. The dental tool of claim 1, further comprising an abutment.

20. A dental tool, comprising:
    A head portion, wherein the head portion comprises a sidewall;
    a resilient collar, wherein the resilient collar is received into the head portion, wherein the resilient collar defines a central bore sized to receive an abutment.

21. The dental tool of claim 20, wherein the sidewall is cylindrically shaped and defines at least one notch.

22. The dental tool of claim 21, wherein the sidewall defines two laterally opposed notches.

* * * * *